United States Patent [19]

Kohl et al.

[11] Patent Number: 5,587,389
[45] Date of Patent: Dec. 24, 1996

[54] SUBSTITUTED HETEROARYLAKLYLTHIOPYRIDINES FOR CONTROLLING HELICOBACTER BACTERIA

[75] Inventors: Bernhard Kohl; Jörg Senn-Bilfinger; Gerhard Grundler, all of Konstanz, Germany

[73] Assignee: BYK Gulden Lomberg Chemische Fabrik GmbH, Konstanz, Germany

[21] Appl. No.: 505,270

[22] PCT Filed: Feb. 11, 1994

[86] PCT No.: PCT/EP94/00393

§ 371 Date: Aug. 15, 1995

§ 102(e) Date: Aug. 15, 1995

[87] PCT Pub. No.: WO94/19346

PCT Pub. Date: Sep. 1, 1994

[30] Foreign Application Priority Data

Feb. 17, 1993 [CH] Switzerland ............... 00507/93

[51] Int. Cl.[6] ............ A61K 31/415; A61K 31/44; C07D 213/70; C07D 233/42
[52] U.S. Cl. .............. 514/338; 514/333; 546/273.4
[58] Field of Search ............... 546/271, 273.4; 514/338, 333

[56] References Cited

U.S. PATENT DOCUMENTS

| 4,628,098 | 12/1986 | Nohara | 546/271 |
| 5,045,552 | 9/1991 | Souda | 514/338 |
| 5,504,082 | 4/1996 | Kawakita | 514/234.5 |

*Primary Examiner*—C. Warren Ivy
*Assistant Examiner*—D. Margaret M. Mach
*Attorney, Agent, or Firm*—Jacobson, Price, Holman & Stern, PLLC

[57] ABSTRACT

Substituted heteroarylalkylthiopyridines of the formula (I)

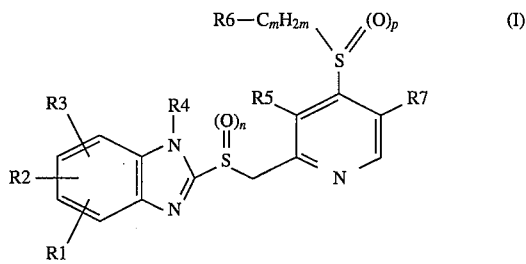

are suitable for treating conditions caused by Helicobacter bacteria, in particular the strain Helicobacter pylori.

10 Claims, No Drawings

SUBSTITUTED HETEROARYLAKLYLTHIOPYRIDINES FOR CONTROLLING HELICOBACTER BACTERIA

This application is a 371 of PCT/EP94/00393, filed 11 Feb., 1996.

FIELD OF THE INVENTION

The invention relates to compounds which are to be used in the pharmaceutical industry as active ingredients for the preparation of drug products.

KNOWN TECHNICAL BACKGROUND

European Patent Application 150,586 discloses 2-(pyridylmethylthio- or sulfinyl)benzimidazoles which can be substituted in the pyridine moiety of the molecule in the 4-position by, inter alia, alkylthio or arylthio radicals. It is mentioned that the above-described compounds have a sustained inhibitory action on the secretion of gastric acid. International Patent Application WO 89/03830 describes that the same compounds, and others having a similar structure, are suitable for treating osteoporosis. International Patent Application WO 92/12976 describes 2-(pyridylmethylthio- or sulfinyl)benzimidazoles which are substituted in a certain manner, which are active against Helicobacter bacteria and which are furthermore disclosed as being suitable for preventing and treating a wide range of stomach disorders.

DESCRIPTION OF THE INVENTION

The invention relates to compounds of the formula I (see appended formula sheet) in which R1 is hydrogen, 1–4C-alkyl or 1–4C-alkoxy, R2 is hydrogen, 1–4C-alkyl, 1–4C-alkoxy, halogen, trifluoromethyl, fully or predominantly fluorine-substituted 1–4C-alkoxy, chlorodifluoromethoxy, 2-chloro-1,1,2-trifluoroethoxy, or, if desired, together with R3 1–2C-alkylenedioxy which is fully or partially substituted by fluorine, or chlorotrifluoroethylenedioxy, R3 is hydrogen, 1–4C-alkoxy which is fully or predominantly substituted by fluorine, or is chlorodifluoromethoxy, 2-chloro-1,1,2-trifluoroethoxy, or, if desired, together with R2 1–2C-alkylenedioxy which is fully or partially substituted by fluorine, or chlorotrifluoroethylenedioxy, R4 is hydrogen or 1–4C-alkyl, R5 is hydrogen, 1–4C-alkyl or 1–4C-alkoxy, R6 is a heterocycle selected from the group consisting of furan, thiophene, pyrrole, oxazole, isoxazole, thiazole, isothiazole, imidazole, pyrazole, 1,2,3-triazole, 1,2,4-triazole, tetrazole, 1,3,4-thiadiazole, 1,2,4-thiadiazole, pyrimidine and pyridine, each o#which is substituted by R8 and R9, R7 is hydrogen, 1–4C-alkyl or 1–4C-alkoxy, R8 is hydrogen, 1–4C-alkyl, 1–4C-alkoxy, halogen, guanidino, 1–4C-alkyl which is substituted by R10, or —N(R11)R12, R9 is hydrogen, 1–4C-alkyl, 1–4C-alkoxy or halogen, R10 is hydroxyl, 1–4C-alkoxy or —N(R11)R12, where R11 is hydrogen, 1–4C-alkyl or —CO-R13 and R12 is hydrogen or 1–4C-alkyl, or where R11 and R12 together and including the nitrogen atom to which both are bonded represent a piperidino or morpholino radical, R13 is hydrogen, 1–4C-alkyl or 1-4C-alkoxy, m is a number from 1 to 7, n is the number 0 or 1 and p is the number 0 or 1, and the salts thereof.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1–4C-Alkoxy represents a radical which, in addition to the oxygen atom, contains one of the above-mentioned 1–4C-alkyl radicals. Examples which may be mentioned are the methoxy and ethoxy radicals.

Halogen for the purposes of the invention is bromine, chlorine and fluorine.

Examples which may be mentioned of 1–4C-alkoxy which is fully or predominantly substituted by fluorine are the 1,2,2-trifluoroethoxy, the 2,2,3,3,3-pentafluoropropoxy, the perfluoroethoxy and, in particular, the 1,1,2,2-tetrafluoroethoxy, the trifluoromethoxy, the 2,2,2-trifluoroethoxy and the difluoromethoxy radicals.

Examples which may be mentioned of 1–2C-alkylenedioxy which is optionally fully or partially substituted by fluorine are the methylenedioxy(—O—$CH_2$—O—), the ethylenedioxy(—O—$CH_2$—$CH_2$—O—), the 1,1-difluoroethylenedioxy(—O—CF2—$CH_2$—O—), the 1,1,2,2-tetrafluoroethylenedioxy(—O—$CF_2$—$CF_2$—O—) and, in particular, the difluoromethylenedioxy(—O—$CF_2$—O—) and the 1,1,2-trifluoroethylenedioxy radicals (—O—$CF_2$-CHF—O—).

If R2 and R3 together are 1–2C-alkylenedioxy which is optionally fully or partially substituted by fluorine, or are chlorotrifluoroethylenedioxy, then the substituents R2 and R3 are bonded on the benzo moiety of the benzimidaizole ring in adjacent positions, preferably in the 5- and 6-positions.

The heterocycles R6 can be bonded to the radical —$C_mH_{2m}$—via any conceivable position, so that examples of radicals R6 which may be mentioned are the following: 2-furyl, 3-furyl, 2-thienyl, 3-thienyl, 1-pyrrolyl, 2-pyrrolyl, 3-pyrrolyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 3-isothiazolyl, 4-isothiazolyl, 5-isothiazolyl, 1-imidazolyl, 2-imidazolyl, 4-imidazolyl, 1-pyrazolyl, 3-pyrazolyl, 4-pyrazolyl, 1,2,3-triazol-l-yl, 1,2,3-triazol-2-yl, 1,2,3-triazol-4-yl, 1,2,4-triazol-l-yl, 1,2,4-triazol-3-yl, 1,2,4-triazol-4-yl, tetrazol-1-yl, tetrazol-2-yl, tetrazol-5-yl, 1,3,4-thiadiazol-2-yl, 1,2,4-thiadiazol-3-yl, 2-pyridinyl, 4-pyridinyl and 2-pyrimidinyl.

The substituents R8 and, if appropriate, R9 can be bonded to the heterocycles R6 in any conceivable position. Examples which may be mentioned of substituted heterocycles R6 are the following radicals: 3-methyl-2-furyl, 2-methyl-3-furyl, 5-methyl-2-furyl, 5-ethyl-2-furyl, 2-dimethylaminomethyl-5-methyl-3-furyl, 3-methoxy-2-furyl, 5-dimethylaminomethyl-2-furyl, 5-N-morpholinomethyl-2-furyl, 5-methoxymethyl-2-furyl, 5-hydroxymethyl-2-furyl, 5—N-piperidinomethyl-2-furyl, 5-chloro-2-furyl, 5-fluoro-2-furyl, 5-methyl-2-thienyl, 5-chloro-2-thienyl, 3-methyl-2-thienyl, 3-amino-2-thienyl, 3-guanidino-2-thienyl, 3-methoxy-2-thienyl, 2-methyl-3-thienyl, 5-dimethylaminomethyl-2-thienyl, 5-N-morpholinomethyl-2-thienyl, 5-methyl-2-pyrrolyl, 2,5-dimethyl-l-pyrrolyl, 1,5-dimethyl-2-pyrrolyl, 1-methyl-2-pyrrolyl, 2-amino-4-thiazolyl, 2-methyl-4-thiazolyl, 2-amino-5-methyl-4-thiazolyl, 4-methyl-5-thiazolyl, 2-dimethylaminomethyl-4-thiazolyl, 4,5-dimethyl-2-thiazolyl, 2-guanidino-4-thiazolyl, 2-formylamino-4-thiazolyl, 2-N-morpholinomethyl-4-thiazolyl, 4-methyl-5-oxazolyl, 3-guanidino-1-pyrazolyl, 3-guanidino-4-pyrazolyl, 2-methyl-4-imidazolyl, 5-methyl-4-imidazolyl, 2-methyl-1-imidazolyl, 4,5-dimethyl-2-imidazolyl, 4-hydroxymethyl-5-methyl-1-imidazolyl, 3-methyl-1-pyrazolyl, 5-amino-1,2,4-thiadiazol-3-yl, 4-methoxy-2-pyridinyl, 4-methoxy-3-methyl-2-pyridinyl and 3,4-dimethoxypyridinyl.

Suitable radicals —$C_mH_{2m}$— which are substituted by R6 are straight-chain or branched radicals. Examples which may be mentioned are the heptyl, isoheptyl-(2-methylhexyl), hexyl, isohexyl-(2-methylpentyl), neohexyl-(2,2-dimethylbutyl), pentyl, isopentyl-(3-methylbutyl), neopentyl-(2,2-dimethylpropyl), butyl, isobutyl, sec-butyl, tert-butyl, propyl, isopropyl, ethyl and methyl radicals. Examples of radicals —$C_mH_{2m}$-R6 which will be mentioned are the radicals: 3-methyl-2-furyl-methyl, 3-methyl-2-furyl-ethyl, 2-furyl-methyl, 2-furyl-ethyl, 2-furyl-propyl, 2-furyl-butyl, 5-dimethylaminomethyl-2-furyl-methyl, 5-dimethylaminomethyl-2-furyl-ethyl, 5-dimethylaminomethyl-2-furyl-propyl, 2-methyl-3-furyl-methyl, 2-methyl-3-furyl-ethyl, 5-N-morpholinomethyl-2-furyl-methyl, 5—N-morpholinomethyl-2-furyl-ethyl, 5-N-piperidinomethyl-2-furyl-methyl, 5-N-piperidinomethyl-2-furyl-ethyl, 3-methoxy-2-furyl-methyl, 3-methoxy-2-furyl-ethyl, 3-amino-2-thienyl-methyl, 3-amino-2-thienyl-ethyl, 3-guanidino-2-thienyl-methyl, 5-dimethylaminomethyl-2-thienyl-methyl, 5-N-morpholinomethyl-2-thienyl-methyl, 1-methyl-2-pyrrolyl-methyl, 2-amino-4-thiazolyl-methyl, 2-dimethylaminomethyl-4-thiazolyl-methyl, 2-guanidino-4-thiazolyl-methyl, 2-N-morpholinomethyl-4-thiazolylmethyl, 5-methyl-4-imidazolyl-methyl, 4-hydroxymethyl-5-methyl-1-imidazolyl-methyl, 3-guanidino-2-thienyl-ethyl, 5-dimethylaminomethyl-2-thienyl-ethyl, 5N-morpholinomethyl-2-thienyl-ethyl, 1-methyl-2-pyrrolyl-ethyl, 2-amino-4-thiazolyl-ethyl, 2-dimethylaminomethyl-4-thiazolyl-ethyl, 2-guanidino-4-thiazolyl-ethyl, 2-N-morpholinomethyl-4-thiazolyl-ethyl, 5-methyl-4-imidazolyl-ethyl, 4-hydroxymethyl-5-methyl-1-imidazolyl-ethyl, 5-amino-(1,2,4-thiadiazol-3-yl)-methyl and 5-amino-(1,2,4-thiadiazol-3-yl)-ethyl.

Suitable salts for compounds of the formula I in which n is the number 0 are all acid addition salts. Particular mention may be made of the pharmacologically acceptable salts of the inorganic and organic acids conventionally used in pharmaceutical technology. Pharmacologically unacceptable salts, which may initially be obtained as process products for example when preparing the compounds according to the invention on an industrial scale, are converted into pharmacologically acceptable salts by methods known to the expert. Suitable as such are water-soluble and water-insoluble acid addition salts with acids such as hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfo-salicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed when preparing the salts in equimolar or a nonequimolar ratio by weight, depending on whether it is a mono- or polybasic acid and depending on the salt desired.

In the case of compounds of the formula I in which n is the number 1, suitable salts are also salts with bases. Examples which may be mentioned of basic salts are the lithium, sodium, potassium, calcium, aluminum, magnesium, titanium, ammonium, meglumine or guanidinium salts, and, when preparing the salts, the bases again being employed in an equimolar or nonequimolar ratio by weight.

Compounds of which particular mention must be made are mentioned in the subclaims.

Compounds which are to be emphasized particularly are those of the formula I in which R1 is hydrogen, R2 is hydrogen, 1–4C-alkoxy, trifluoromethyl, 1–4C-alkoxy which is fully or predominantly substituted by fluorine, or together with R3 is 1–2C-alkylenedioxy which is fully or partially substituted by fluorine, R3 is hydrogen or together with R2 is 1–2C-alkylenedioxy which is fully or partially substituted by fluorine, R4 is hydrogen, R5 is hydrogen, 1–4C-alkyl or 1–4C-alkoxy, R6 is a heterocycle which is selected from the group consisting of furan, thiophene, thiazole, imidazole and pyridine and which is substituted by R8 and R9, R7 is hydrogen, R8 is hydrogen, 1–4C-alkyl or 1–4C-alkoxy or 1–4C-alkyl which is substituted by R10, R9 is hydrogen or 1–4C-alkoxy, R10 is —N(R11)R12, where R11 is 1–4C-alkyl and R12 is 1–4C-alkyl, m is a number from 1 to 3, n is the number 0 or 1 and p is the number 0, and the salts thereof.

Compounds which are to be emphasized particularly are those of the formula I in which R1 is hydrogen, R2 is hydrogen or methoxy, R3 is hydrogen, R4 is hydrogen, R5 is hydrogen, 1–4C-alkyl or 1–4C-alkoxy, R6 is a heterocycle which is selected from the group consisting of furan, thiophene, thiazole, imidazole and pyridine and which is substituted by R8 and R9, R7 is hydrogen, R8 is hydrogen, 1–4C-alkyl, 1–4C-alkoxy or 1–4C-alkyl which is substituted by R10, R9 is hydrogen or 1–4C-alkoxy, R10 is —N(R11)R12, where R11 is 1–4C-alkyl and R12 is 1–4C-alkyl, m is a number from 1 to 3, n is the number 0 and p is the number 0, and the salts thereof.

Examples of compounds according to the invention are listed in Table 1 which follows:

TABLE 1

Compounds of the formula I (see appended formula sheet) where the substituents have the following meanings:

| R1 | R2 | R3 | R4 | R5 | R6 | R7 | m | n | p |
|---|---|---|---|---|---|---|---|---|---|
| H | H | H | H | H | 2-Furyl | H | 1 | 0 | 0 |
| H | H | H | H | H | 2-Thienyl | H | 1 | 0 | 0 |
| H | H | H | H | H | 3-Thienyl | H | 1 | 0 | 0 |
| H | H | H | H | H | 5-Dimethylaminomethyl-2-furyl | H | 1 | 0 | 0 |
| H | H | H | H | H | 5-Piperidinomethyl-2-furyl | H | 1 | 0 | 0 |
| H | H | H | H | H | 5-Dimethylaminomethyl-2-thienyl | H | 1 | 0 | 0 |
| H | H | H | H | H | 2-Amino-4-thiazolyl | H | 1 | 0 | 0 |
| H | H | H | H | H | 2-Dimethylaminomethyl-4-thiazolyl | H | 1 | 0 | 0 |
| H | H | H | H | H | 2-Guanidino-4-thiazolyl | H | 1 | 0 | 0 |
| H | H | H | H | H | 2-Formylamino-4-thiazolyl | H | 1 | 0 | 0 |
| H | H | H | H | H | 4-Methyl-5-oxazolyl | H | 1 | 0 | 0 |
| H | H | H | H | H | 2-Methyl-4-imidazolyl | H | 1 | 0 | 0 |
| H | H | H | H | H | 5-Methyl-4-imidazolyl | H | 1 | 0 | 0 |
| H | H | H | H | H | 5-Amino-1,2,4-thiadiazol-3-yl | H | 1 | 0 | 0 |
| H | F | H | H | H | 2-Furyl | H | 1 | 0 | 0 |
| H | OCH$_3$ | H | H | H | 2-Furyl | H | 1 | 0 | 0 |
| H | OCH$_3$ | H | H | H | 2-Thienyl | H | 1 | 0 | 0 |
| H | OCH$_3$ | H | H | H | 5-Dimethylaminomethyl-2-furyl | H | 1 | 0 | 0 |
| H | OCH$_3$ | H | H | H | 5-Dimethylaminomethyl-2-thienyl | H | 1 | 0 | 0 |
| H | OCH$_3$ | H | H | H | 2-Amino-4-thiazolyl | H | 1 | 0 | 0 |
| H | OCH$_3$ | H | H | H | 2-Dimethylaminomethyl-4-thiazolyl | H | 1 | 0 | 0 |
| H | OCH$_3$ | H | H | H | 2-Guanidino-4-thiazolyl | H | 1 | 0 | 0 |
| H | OCH$_3$ | H | H | H | 2-Formylamino-4-thiazolyl | H | 1 | 0 | 0 |
| H | OCH$_3$ | H | H | H | 4-Methyl-5-thiazolyl | H | 1 | 0 | 0 |
| H | OCH$_3$ | H | H | H | 4-Methyl-5-oxazolyl | H | 1 | 0 | 0 |
| H | OCH$_3$ | H | H | H | 2-Methyl-4-imidazolyl | H | 1 | 0 | 0 |
| H | OCH$_3$ | H | H | H | 5-Methyl-4-imidazolyl | H | 1 | 0 | 0 |
| H | H | H | H | CH$_3$ | 2-Furyl | H | 1 | 0 | 0 |
| H | H | H | H | CH$_3$ | 2-Thienyl | H | 1 | 0 | 0 |
| H | H | H | H | CH$_3$ | 5-Dimethylaminomethyl-2-furyl | H | 1 | 0 | 0 |
| H | H | H | H | CH$_3$ | 5-Dimethylaminomethyl-2-thienyl | H | 1 | 0 | 0 |
| H | H | H | H | CH$_3$ | 2-Amino-4-thiazolyl | H | 1 | 0 | 0 |
| H | H | H | H | CH$_3$ | 2-Dimethylaminomethyl-4-thiazolyl | H | 1 | 0 | 0 |
| H | H | H | H | CH$_3$ | 2-Guanidino-4-thiazolyl | H | 1 | 0 | 0 |
| H | H | H | H | CH$_3$ | 2-Formylamino-4-thiazolyl | H | 1 | 0 | 0 |
| H | H | H | H | CH$_3$ | 4-Methyl-5-oxazolyl | H | 1 | 0 | 0 |
| H | H | H | H | CH$_3$ | 2-Methyl-4-imidazolyl | H | 1 | 0 | 0 |
| H | H | H | H | CH$_3$ | 5-Methyl-4-imidazolyl | H | 1 | 0 | 0 |
| H | F | H | H | CH$_3$ | 2-Furyl | H | 1 | 0 | 0 |
| H | H | H | H | OCH$_3$ | 2-Furyl | H | 1 | 0 | 0 |
| H | H | H | H | OCH$_3$ | 2-Thienyl | H | 1 | 0 | 0 |
| H | H | H | H | OCH$_3$ | 5-Dimethylaminomethyl-2-furyl | H | 1 | 0 | 0 |
| H | H | H | H | OCH$_3$ | 5-Dimethylaminomethyl-2-thienyl | H | 1 | 0 | 0 |
| H | H | H | H | OCH$_3$ | 2-Amino-4-thiazolyl | H | 1 | 0 | 0 |
| H | H | H | H | OCH$_3$ | 2-Dimethylaminomethyl-4-thiazolyl | H | 1 | 0 | 0 |
| H | H | H | H | OCH$_3$ | 2-Guanidino-4-thiazolyl | H | 1 | 0 | 0 |
| H | H | H | H | OCH$_3$ | 2-Formylamino-4-thiazolyl | H | 1 | 0 | 0 |
| H | H | H | H | OCH$_3$ | 4-Methyl-5-oxazolyl | H | 1 | 0 | 0 |
| H | H | H | H | OCH$_3$ | 2-Methyl-4-imidazolyl | H | 1 | 0 | 0 |
| H | H | H | H | OCH$_3$ | 5-Methyl-4-imidazolyl | H | 1 | 0 | 0 |
| H | F | H | H | OCH$_3$ | 2-Furyl | H | 1 | 0 | 0 |
| H | H | H | H | H | 2-Furyl | H | 2 | 0 | 0 |
| H | H | H | H | H | 2-Thienyl | H | 2 | 0 | 0 |
| H | H | H | H | H | 5-Dimethylaminomethyl-2-furyl | H | 2 | 0 | 0 |
| H | H | H | H | H | 5-Dimethylaminomethyl-2-thienyl | H | 2 | 0 | 0 |
| H | H | H | H | H | 2-Amino-4-thiazolyl | H | 2 | 0 | 0 |
| H | H | H | H | H | 2-Dimethylaminomethyl-4-thiazolyl | H | 2 | 0 | 0 |
| H | H | H | H | H | 2-Guanidino-4-thiazolyl | H | 2 | 0 | 0 |
| H | H | H | H | H | 2-Formylamino-4-thiazolyl | H | 2 | 0 | 0 |
| H | H | H | H | H | 4-Methyl-5-oxazolyl | H | 2 | 0 | 0 |
| H | H | H | H | H | 2-Methyl-4-imidazolyl | H | 2 | 0 | 0 |
| H | H | H | H | H | 5-Methyl-4-imidazolyl | H | 2 | 0 | 0 |
| H | OCH$_3$ | H | H | H | 2-Furyl | H | 2 | 0 | 0 |
| H | OCH$_3$ | H | H | H | 2-Thienyl | H | 2 | 0 | 0 |
| H | OCH$_3$ | H | H | H | 5-Dimethylaminomethyl-2-furyl | H | 2 | 0 | 0 |
| H | OCH$_3$ | H | H | H | 5-Dimethylaminomethyl-2-thienyl | H | 2 | 0 | 0 |
| H | OCH$_3$ | H | H | H | 2-Amino-4-thiazolyl | H | 2 | 0 | 0 |
| H | OCH$_3$ | H | H | H | 2-Dimethylaminomethyl-4-thiazolyl | H | 2 | 0 | 0 |
| H | OCH$_3$ | H | H | H | 2-Guanidino-4-thiazolyl | H | 2 | 0 | 0 |
| H | OCH$_3$ | H | H | H | 2-Formylamino-4-thiazolyl | H | 2 | 0 | 0 |
| H | OCH$_3$ | H | H | H | 4-Methyl-5-oxazolyl | H | 2 | 0 | 0 |
| H | OCH$_3$ | H | H | H | 2-Methyl-4-imidazolyl | H | 2 | 0 | 0 |
| H | OCH$_3$ | H | H | H | 5-Methyl-4-imidazolyl | H | 2 | 0 | 0 |
| H | H | H | H | CH$_3$ | 2-Furyl | H | 2 | 0 | 0 |

TABLE 1-continued

Compounds of the formula I (see appended formula sheet) where the substituents have the following meanings:

| R1 | R2 | R3 | R4 | R5 | R6 | R7 | m | n | p |
|---|---|---|---|---|---|---|---|---|---|
| H | H | H | H | CH₃ | 2-Thienyl | H | 2 | 0 | 0 |
| H | H | H | H | CH₃ | 5-Dimethylaminomethyl-2-furyl | H | 2 | 0 | 0 |
| H | H | H | H | CH₃ | 5-Dimethylaminomethyl-2-thienyl | H | 2 | 0 | 0 |
| H | H | H | H | CH₃ | 2-Amino-4-thiazolyl | H | 2 | 0 | 0 |
| H | H | H | H | CH₃ | 2-Dimethylaminomethyl-4-thiazolyl | H | 2 | 0 | 0 |
| H | H | H | H | CH₃ | 2-Guanidino-4-thiazolyl | H | 2 | 0 | 0 |
| H | H | H | H | CH₃ | 2-Formylamino-4-thiazolyl | H | 2 | 0 | 0 |
| H | H | H | H | CH₃ | 4-Methyl-5-oxazolyl | H | 2 | 0 | 0 |
| H | H | H | H | CH₃ | 2-Methyl-4-imidazolyl | H | 2 | 0 | 0 |
| H | H | H | H | CH₃ | 5-Methyl-4-imidazolyl | H | 2 | 0 | 0 |
| H | H | H | H | OCH₃ | 2-Furyl | H | 2 | 0 | 0 |
| H | H | H | H | OCH₃ | 2-Thienyl | H | 2 | 0 | 0 |
| H | H | H | H | OCH₃ | 5-Dimethylaminomethyl-2-furyl | H | 2 | 0 | 0 |
| H | H | H | H | OCH₃ | 5-Dimethylaminomethyl-2-thienyl | H | 2 | 0 | 0 |
| H | H | H | H | OCH₃ | 2-Amino-4-thiazolyl | H | 2 | 0 | 0 |
| H | H | H | H | OCH₃ | 2-Dimethylaminomethyl-4-thiazolyl | H | 2 | 0 | 0 |
| H | H | H | H | OCH₃ | 2-Guanidino-4-thiazolyl | H | 2 | 0 | 0 |
| H | H | H | H | OCH₃ | 2-Formylamino-4-thiazolyl | H | 2 | 0 | 0 |
| H | H | H | H | OCH₃ | 4-Methyl-5-oxazolyl | H | 2 | 0 | 0 |
| H | H | H | H | OCH₃ | 2-Methyl-4-imidazolyl | H | 2 | 0 | 0 |
| H | H | H | H | OCH₃ | 5-Methyl-4-imidazolyl | H | 2 | 0 | 0 |
| H | OCH₃ | H | H | H | 3-Thienyl | H | 1 | 0 | 0 |
| H | H | H | H | CH₃ | 3-Thienyl | H | 1 | 0 | 0 |
| H | H | H | H | OCH₃ | 3-Thienyl | H | 1 | 0 | 0 |
| H | H | H | H | H | 3-Thienyl | H | 2 | 0 | 0 |
| H | OCH₃ | H | H | H | 3-Thienyl | H | 2 | 0 | 0 |
| H | H | H | H | CH₃ | 3-Thienyl | H | 2 | 0 | 0 |
| H | H | H | H | OCH₃ | 3-Thienyl | H | 2 | 0 | 0 |
| H | OCH₃ | H | H | H | 5-Piperidinomethyl-2-furyl | H | 1 | 0 | 0 |
| H | H | H | H | CH₃ | 5-Piperidinomethyl-2-furyl | H | 1 | 0 | 0 |
| H | H | H | H | OCH₃ | 5-Piperidinomethyl-2-furyl | H | 1 | 0 | 0 |
| H | H | H | H | H | 5-Piperidinomethyl-2-furyl | H | 2 | 0 | 0 |
| H | OCH₃ | H | H | H | 5-Piperidinomethyl-2-furyl | H | 2 | 0 | 0 |
| H | H | H | H | CH₃ | 5-Piperidinomethyl-2-furyl | H | 2 | 0 | 0 |
| H | H | H | H | OCH₃ | 5-Piperidinomethyl-2-furyl | H | 2 | 0 | 0 |
| H | OCH₃ | H | H | H | 5-Amino-1,2,4-thiadiazol-3-yl | H | 1 | 0 | 0 |
| H | H | H | H | CH₃ | 5-Amino-1,2,4-thiadiazol-3-yl | H | 1 | 0 | 0 |
| H | H | H | H | OCH₃ | 5-Amino-1,2,4-thiadiazol-3-yl | H | 1 | 0 | 0 |
| H | H | H | H | H | 5-Amino-1,2,4-thiadiazol-3-yl | H | 2 | 0 | 0 |
| H | OCH₃ | H | H | H | 5-Amino-1,2,4-thiadiazol-3-yl | H | 2 | 0 | 0 |
| H | H | H | H | CH₃ | 5-Amino-1,2,4-thiadiazol-3-yl | H | 2 | 0 | 0 |
| H | H | H | H | OCH₃ | 5-Amino-1,2,4-thiadiazol-3-yl | H | 2 | 0 | 0 |
| H | H | H | H | H | 4-Methyl-5-thiazolyl | H | 1 | 0 | 0 |
| H | H | H | H | CH₃ | 4-Methyl-5-thiazolyl | H | 1 | 0 | 0 |
| H | H | H | H | OCH₃ | 4-Methyl-5-thiazolyl | H | 1 | 0 | 0 |
| H | H | H | H | H | 4-Methyl-5-thiazolyl | H | 2 | 0 | 0 |
| H | OCH₃ | H | H | H | 4-Methyl-5-thiazolyl | H | 2 | 0 | 0 |
| H | H | H | H | CH₃ | 4-Methyl-5-thiazolyl | H | 2 | 0 | 0 |
| H | H | H | H | OCH₃ | 4-Methyl-5-thiazolyl | H | 2 | 0 | 0 | and the salts of these compounds.

The invention furthermore relates to a process for the preparation of the compounds of the formula I in which R1, R2, R3, R4, R5, R6, R7, m, n and p have the abovementioned meanings, and of the salts thereof.

The process comprises reacting mercaptobenzimidazoles of the formula II (see appended formula sheet), in which R1, R2, R3 and R4 are as defined above, with picoline derivatives III (see appended formula sheet), in which R5, R6, R7, m and p are as defined above and X represents a suitable leaving group, and (if the desired end products are compounds of the formula I where n=1) subsequently oxidizing the resulting 2-benzimidazolyl-2-pyridylmethyl sulfides of the formula I where n=0 and/or, if desired, converting them into the salts.

In the above-mentioned reaction, the compounds II and III can be employed as such or, if appropriate, in the form of their salts.

The reaction of II with III is carried out in suitable, preferably polar, protic or aprotic, solvents (such as methanol, isopropanol, dimethyl sulfoxide, acetone, dimethylformamide or acetonitrile) with the addition or exclusion of water. It is carried out, for example, in the presence of a proton acceptor. Suitable proton acceptors are alkali metal hydroxides, such as sodium hydroxide, alkali metal carbonates, such as potassium carbonate, or tertiary amines, such as pyridine, triethylamine or ethyldiisopropylamine.

Alternatively, the reaction can also be carried out without a proton acceptor, it optionally being possible, depending on the nature of the starting compounds, to first remove the acid addition salts in particularly pure form. The reaction temperature can be between 0° and 150° C., and preferred temperatures are between 20° and 80° C. in the presence of proton acceptors and between 60° and 120° C. without proton acceptors, in particular the boiling point of the solvents used. The reaction times are between 0.5 and 12 hours.

The oxidation of the sulfides (compounds of the formula I where n=0) to the sulfoxides (compounds of the formula I where n=1) is carried out under the conditions which are known to the expert for the oxidation of sulfides to sulfoxides [see, in this context, for example J. Drabowicz and M. Mikolajczyk, Organic preparations and procedures int. 14(1–2), 45–89(1982) or E. Block in S. Patai, The Chemistry of Functional Groups, Supplement E. Part 1, pp. 539–608, John Wiley and Sons (Interscience Publication), 1980]. Oxidants which are suitable are all reagents which are conventionally used for the oxidation of sulfides to sulfoxides, in particular peroxyacids, such as, for example, peroxyacetic acid, trifluoroperoxyacetic acid, 3,5-dinitroperoxybenzoic acid, peroxymaleic acid, magnesium monoperoxyphthalate or, preferably, m-chloroperoxybenzoic acid.

The reaction temperature is (depending on the reactivity of the oxidant and the degree of dilution) between −70° C. and the boiling point of the solvent used, but preferably between −30° and +20° C. Oxidation with halogens or with hypohalites (for example with aqueous sodium hypochlorite solution) has also proved to be advantageous, and this is expediently carried out at temperatures between 0° and 50° C. The reaction is carried out expediently in inert solvents, for example aromatic or chlorinated hydrocarbons, such as benzene, toluene, dichloromethane or chloroform, preferably in esters or ethers, such as ethyl acetate, isopropyl acetate or dioxane, or in alcohols, preferably isopropanol.

The sulfoxides according to the invention are optically active compounds. Depending on the nature of the substituents, the molecule can additionally contain other chiral centers. The invention therefore embraces the enantiomers and diastereomers and also their mixtures and racemates. The enantiomers can be separated in a manner known per se (for example by preparing and separating corresponding diastereoisomeric compounds) (see, for example, WO 92/08716).

The compounds II are disclosed in, for example, WO 86/02646, EP 134,400 or EP 127,763. The compounds III where p=0 can be prepared, for example, as described in the examples which follow.

For compounds III where p=1, the corresponding 2-hydroxymethyl-4-mercapto-substituted pyridines are oxidized to the sulfoxides, for example with m-chloroperoxybenzoic acid, and the products are subsequently chlorinated, for example with thionyl chloride. Reaction with 2-mercaptobenzimidazoles gives the compounds of the formula I where p=1.

The thiols R6—$C_mH_{2m}$—SH which are required for the preparation of III can be prepared analogously to J. Med. Chem. 14 (1971) 349, for example from the corresponding halogen compounds.

The examples which follow are intended to illustrate the preparation of the compounds according to the invention in greater detail. In particular, the examples are also intended to describe the preparation of selected starting materials by way of example. Equally, other compounds of the formula I and other starting compounds whose preparation is not described explicitly can be prepared analogously or in a manner with which the expert is familiar, using customary process methods. The abbreviation RT represents room temperature, h represents hour(s), m.p. melting point, and decomp. decomposition.

EXAMPLES

End products
1. 2-{[[4-(2-Furylmethylthio)-3-methyl,2-pyridinyl]methyl]thio}-1H-benzimidazole One equivalent (2.92 g) of 2-chloromethyl-4-(2-furylmethylthio)-3-methylpyridine hydrochloride (dissolved in 10 ml of water) is added dropwise at 40° C. in the course of 20 minutes to a solution of 2-mercapto-1H-benzimidazole (1.5 g/10 mmol) in 40 ml of ethanol and 21 ml of 1N sodium hydroxide solution. The mixture is subsequently stirred at 50°–60° C. for 2–3 h and at RT for a further 3–4 h, ethanol is distilled off on a rotary evaporator (1 kPa/40° C.), the residue is extracted 3 times using in each case 20 ml of dichloromethane, and the dichloromethane phase is washed with 0.1N sodium hydroxide solution, dried over potassium carbonate and evaporated fully in vacuo. For purification, the crude product is chromatographed on silica gel (dichloromethane/methanol 20:1 to 3:1); the collected pure fractions are together concentrated in vacuo and crystallized from dichloromethane/diisopropyl ether. The product is subsequently recrystallized from methanol/toluene. Yield: 2.61 g (71%) of the title compound as a colorless solid of m.p. 188°–189° C.

2. 2-{[[4-(2-Furylmethylthio)-3-methoxy-2-pyridinyl]methyl]thio}-1H-benzimidazole Following the procedure described in Example 1, the starting compounds 2-mercapto-1H-benzimidazole and 2-chloromethyl-4-(2-furylmethylthio)-3-methoxypyridine hydrochloride give the title compound as a colorless powder of m.p. 102°–103° C. after chromatography on silica gel followed by crystallization from ethanol/water (yield 68%).

3. 2-{[[3-Methyl-4-[2-(4-methyl-5-thiazolyl)-ethylthio]-2-pyridinyl]methyl]thio}-1H-benzimidazole Following the procedure described in Example 1, the reaction of 2-mercapto-1H-benzimidazole with 2-chloromethyl-3-methyl-4-[2-(4-methyl-5-thiazolyl)ethylthio]pyridine hydrochloride gives the title compound as a colorless solid of m.p. 150°–152° C. following crystallization from dichloromethane/diisopropyl ether.

4. 2-{[[4-[(5-Dimethylaminomethyl-2-furyl)methylthio]-3-methyl-2-pyridinyl]methyl]thio}-1H-benzimidazole Following the procedure described in Example 1, the reaction of 2-mercapto-1H-benzimidazole with 2-chloromethyl-4-{[(5-dimethylaminomethyl-2-furyl)methyl]thio}-3-methylpyridine hydrochloride gives the title compound after chromatography on silica gel (dichloromethane/methanol/triethylamine 9:1:0.1 to 2:1:0.1).

H NMR (CDCl$_3$): δ2.24 (s, 6H); 2.33 (s, 3H); 3.41 (s, 2H); 4.15 (s, 2H); 4.43 (s, 2H); 6.10–6.21 (m, 2H); 7.10–7.25 (m, 3H); 7.40–7.60 (m, 2H); 8.27 (d, J=5.4 Hz, 1H).

Dissolving the product in isopropanol, adding aqueous concentrated hydrochloric acid, evaporating the mixture to dryness and crystallization of the residue from methanol/acetone give a hydrochloride salt of the title compound as a colorless crystal powder of m.p. 218° C. (decomp.).

The following compounds are prepared analogously:
5. 2-{[[3-Methyl-4-(2-thienylmethylthio)-2-pyridinyl]methyl]thio}-1H-benzimidazole 2-Chloromethyl-3-methyl-4-(2-thienylmethylthio)pyridine hydrochloride, 2-mercapto-1H-benzimidazole and sodium hydroxide are reacted in ethanol at 25° C. for 20 h. After crystallization from toluene/methanol, the title compound is isolated. Yield: 75%, m.p. 131°–133° C.

6. 2-{[[3-Methyl-4-(3-thienylmethylthio)-2-pyridinyl]methyl]thio}-1H-benzimidazole 2-Chloromethyl-3-methyl-4-(3-thienylmethylthio)pyridine hydrochloride, 2-mercapto-1H-benzimidazole and sodium hydroxide are reacted in ethanol at 25° C. for 20 h. After crystallization from toluene/methanol, the title compound is isolated. Yield: 62%, m.p. 161°–164° C.

7. 2-{[[3-Methoxy-4-(2-thienylmethylthio]-2-pyridinyl]methyl]thio}-1H-benzimidazole 2-Chloromethyl-3-methoxy-4-(2-thienylmethylthio)pyridine hydrochloride, 2-mercapto-1H-benzimidazole and sodium hydroxide are reacted in ethanol at 25° C. for 20 h. After crystallization from toluene/methanol, the title compound is isolated. Yield: 56%, m.p. 124°–127° C.
8. 2-{[[4-(2-Thienylmethylthio)-2,pyridinyl]methyl]thio}-1H-benzimidazole 2-Chloromethyl-4-(2-thienylmethylthio)-pyridine hydrochloride, 2-mercapto-1H-benzimidazole and sodium hydroxide are reacted in ethanol at 60° C. for 5 h. After crystallization from toluene/methanol, the title compound is isolated. Yield: 69%, m.p. 221°–222° C. (decomp.).
9. 2-{[[4-(2-Furylmethylthio)-2-pyridinyl]methyl]thio}-1H-benzimidazole 2-Chloromethyl-4-(2-furylmethylthio)-pyridine hydrochloride, 2-mercapto-1H-benzimidazole and sodium hydroxide are reacted in ethanol at 60° C. for 5 h. After crystallization from toluene/methanol, the title compound is isolated. Yield: 73%, m.p. 208°–209° C.
10. 5-Methoxy-2-{[[4-(2-furylmethylthio)-3-methyl-2-pyridinyl]methyl]thio}-1H-benzimidazole 2-Chloromethyl-4-(2-furylmethylthio)-3-methylpyridine hydrochloride, 5-methoxy-2-mercapto-1H-benzimidazole and sodium hydroxide are reacted in ethanol at 60° C. for 4 h. This gives the title compound as a colorless solid. Yield: 81%, m.p. 106–108° C.
11. 5-Methoxy-2-{[[3-methyl-4-[2-(4-methyl-5-thiazolyl)ethylthio]-2-pyridinyl]methyl]thio}-1H-benzimidazole Following the procedure described in Example 1, the reaction of 5-methoxy-2-mercapto-1H-benzimidazole with 2-chloromethyl-3-methyl-4-[2-(4-methyl-5-thiazolyl)ethylthio]pyridine hydrochloride and aqueous sodium hydroxide solution gives the title compound as a yellow oil, from which a hydrochloride salt of the title compound is obtained as a colorless powder of m.p. 165° C (decomp.) by following the procedure described in Example 4.
12. 2-{[[4-(2-Furylmethylthio)-3-methyl-2-pyridinyl]methyl]thio}-1H-benzimidazole dihydrochloride The compound of Example 1 can also be prepared via the corresponding dihydrochloride, by refluxing 2-mercapto-1H-benzimidazole (1.5 g/10 mmol) in 30 ml of isopropanol with 2-chloromethyl-4-(2-furylmethylthio)-3-methylpyridine hydrochloride (10 mmol) for 5 h, cooling, removing the precipitated solid by filtration and recrystallizing this from isopropanol/water. This gives the title compound (yield 90%) as a colorless solid of m.p. 208° C. (decomp.).
13. 2-{[[4-(2-furylmethylthio)-3-methyl-2-pyridinyl]methyl]thio}-5-trifluoromethyl-1H-benzimidazole dihydrochloride Following the procedure described in Example 12, the reaction of 2-chloromethyl-4-(2-furylmethylthio)-3-methylpyridine hydrochloride with 2-mercapto-5-trifluoromethyl-1H-benzimidazole in isopropanol gives the title compound as a colorless solid; m.p. 173° C (decomp.).
14. 2-{[[4-(2-Furylmethylthio)-3-methyl-2-pyridinyl]methyl]thio}-5-(2,2,2-trifluoroethoxy)-1H-benzimidazole dihydrochloride Following the procedure described in Example 12, the reaction of 2-chloromethyl-4-(2-furylmethylthio)-3-methylpyridine hydrochloride with 2-mercapto-5-(2,2,2-trifluoroethoxy)-1H-benzimidazole in isopropanol gives the title compound as a colorless solid; m.p. 161°–163° C. (decomp.).
15. 2,2-Difluoro-6-{[[4-(2-furylmethylthio)-3-methyl-2-pyridinyl]methyl]thio}-5H-[1,3]dioxolo-[4,5-f]benzimidazole dihydrochloride Following the procedure described in Example 12, the reaction of 2-chloromethyl-4-(2-furylmethylthio)-3-methylpyridine hydrochloride with 2,2-difluoro-6-mercapto-5H-[1,3]dioxolo-[4,5-f]benzimidazole in isopropanol gives the title compound as a colorless solid; m.p. 180–183° C. (decomp.).
16. 2-{[[4-3,4-Dimethoxy-2-pyridinylmethylthiol-3-methyl-2-pyridinyl]methyl]thio}-1H-benzimidazole Following the procedure described in Example 1, the reaction of 2-mercapto-1H-benzimidazole with 2-chloromethyl-4-[(3,4-dimethoxy)-2-pyridinylmethylthio]-3-methylpyridine hydrochloride in ethanol with an addition of sodium hydroxide solution gives a yellow oil. Crystallization from ethyl acetate yields the title compound as a colorless solid of m.p. 165°–167° C.
17. 2{([[4-(2-Pyridinyl-2-ethylthio)-3-methyl-2-pyridinyl]methyl]thio}-1H-benzimidazole Following the procedure described in Example 1, the reaction of 2-mercapto-1H-benzimidazole with 2-chloromethyl-4-(2-pyridinyl-2-ethylthio)-3-methylpyridine hydrochloride gives the title compound after crystallization from diisopropyl ether; m.p. 147°–149° C.
18. 2-{[[-4-[3-(Imidazol-1-yl)propylthio]-3-methyl-2-pyridinyl]methyl]thio}-1H-benzimidazole Following the procedure described in Example 1, the reaction of 2-mercapto-1H-benzimidazole with 2-chloromethyl-4-[3-(imidazol-1-yl)propylthio]-3-methylpyridine hydrochloride gives the title compound as a colorless solid after crystallization from diisopropyl ether; m.p. 145°–146° C.
19. 2-{[[4-[3-(2-Methylimidazol-1-yl)propylthio]-3-methyl-2-pyridinyl]methyl]thio}-1H-benzimidazole Following the procedure described in Example 1, 2-chloromethyl-4-[3-(2-methylimidazol-1-yl)propylthio]-3-methylpyridine hydrochloride gives the title compound as a yellow oil. Following the procedure described in Example 4, a hydrochloride salt of the title compound of m.p. 212°–215° C. (decomp.) is obtained therefrom.
20. 2-{[[4-(2-Furylmethylthio)-3-methyl-2-pyridinyl]methyl]sulfinyl}-1H-benzimidazole 2-{[[4-(2-Furylmethylthio)-3-methyl-2-pyridinyl]methyl]thio}-1H-benzimidazole (2 mmol) are dissolved in 15 ml of dioxane + NaOH (6 mmol; 2N), and the solution is treated with 2.5 mmol of 7 percent strength sodium hypochlorite solution at 20° C. Sodium thiosulfate is added, dioxane is distilled off, the pH is brought to 9, the mixture is extracted using dichloromethane, and the product is crystallized from dichloromethane/diisopropyl ether. This gives the title compound (yield 80%) of m.p. 173° C. (decomp.) as a colorless solid.

Starting compounds

A. 2-Chloromethyl-4-(2-furylmethylthio)-3-methylpyridine hydrochloride a) 2,3-Dimethyl-4-(2-furylmethylthio)pyridine N-oxide 6 g of (60%) NaOH are added in portions to 50 ml of dry dioxane, the mixture is stirred for 15 minutes, 11.7 g (0.11 mol) of 2-furylmethylmercaptan are metered in, in the course of 20 minutes, and the mixture is again stirred for 30 minutes until the evolution of gas has ceased. A solution of 14.4 g (0.1 mol) of 4-chloro-2,3-dimethylpyridine N-oxide in 100 ml of dioxane is subsequently added dropwise in the course of 20 minutes, the reaction mixture is stirred at RT for 1 h, subsequently at 70° C. for 1 h and thereupon at 100° C. for a further 1 h. After the reaction has ended, the mixture is allowed to cool, diluted with 500 ml of water and extracted 4 times using in each case 300 ml of ethyl acetate. The combined organic phases are washed with water, dried over magnesium sulfate, concentrated and crystallized by adding diisopropyl ether. This gives 18.8 g (80% of theory)

of 2,3-dimethyl-4-(2-furylmethylthio)pyridine N-oxide of m.p. 111°–112° C.

b) 2-Acetoxymethyl-4-(2-furylmethylthio)-3-methylpyridine 18.0 g (0.77 mol) of the product obtained under a) are heated in 100 ml of acetic anhydride (100° C.) and stirred for 2 h. After the mixture has been concentrated in vacuo, the brown oily residue is distilled in a bulb-tube distillation apparatus. This gives 17.0 g of 2-acetoxymethyl-4-(2-furylmethylthio)-3-methylpyridine, which is further reacted directly.

c) 4-(2-Furylmethylthio)-2-hydroxymethyl-3-methylpyridine

The product of b) (17.0 g) is refluxed with stirring for 2 h in 100 ml of 2N sodium hydroxide solution and 100 ml of isopropanol, isopropanol is distilled off, and the residue is extracted 3 times using in each case 100 ml of dichloromethane. The combined organic phases are washed with water, dried over potassium carbonate, and concentrated in vacuo, and the product is crystallized from a little toluene. This gives 13.4 g (93%) of 4-(2-furylmethylthio)-2-hydroxymethyl-3-methylpyridine as a cream solid of m.p. 60°–62° C.

d) 2-Chloromethyl-4-(2-furylmethylthio)-3-methylpyridine hydrochloride 10.0 g (0.042 mol) of 4-(2-furylmethylthio)-2-hydroxymethyl-3-methylpyridine are dissolved in dichloromethane (100 ml), 1.2 equivalents of thionyl chloride are added dropwise at RT, and the mixture is stirred at RT for 20 h. The mixture is concentrated fully, which gives the title compound as an oily residue which crystallizes slowly and which, if desired, can also be used directly as a solution in ethanol for the reaction with substituted 2-mercaptobenzimidazoles. For purification, it is recrystallized from hot isopropanol with an addition of active charcoal. This gives 9.0 g (74% of theory) of the title compound as colorless crystals of m.p. 159°–161° C. (decomp.).

B) 2-Chloromethyl-3-methyl-4-[2-(4-methyl-5-thiazolyl) ethylthio]pyridine hydrochloride a) 2,3-Dimethyl-4-[2-(4-methyl-5-thiazolyl)-ethylthio]pyridine N-oxide Following the procedure described in Example Aa), the reaction of 4-chloro-2,3-dimethylpyridine N-oxide with 5-(2-mercaptoethyl)-4-methylthiazole in the presence of sodium hydride gives 2,3-dimethyl-4-[2-(4-methyl-5-thiazolyl)-ethylthio]pyridine N-oxide; m.p.: 135°–137° C (yield: 79%).

b) 2-Acetoxymethyl-3-methyl-4-[2-(4-methyl-5-thiazolyl)-ethylthio]pyridine

Following the procedure described in Example Ab), product Ba) gives 2-acetoxymethyl-3-methyl-4-[2-(4-methyl-5-thiazolyl)-ethylthio]pyridine as a yellow oil which is further reacted directly.

c) 2-Hydroxymethyl-3-methyl-4-[2-(4-methyl-5-thiazolyl)-ethylthio]pyridine

Following the procedure described under Ac), product Bb) gives the title compound, which is further reacted directly as a crude product without crystallization.

d) 2-Chloromethyl-3-methyl-4-[2-(4-methyl-5-thiazolyl) ethylthio]pyridine hydrochloride Following the procedure described under Ad), product Bc) gives the title compound, which is dissolved in ethanol in the form of the crude product and the solution is further reacted directly.

C) 2-Chloromethyl-4-{[5-dimethylaminomethyl-2-furyl)methyl]thio}-3-methylpyridine hydrochloride a) 4-{[(5-Dimethylaminomethyl-2-furyl)methyl]thio}-2-hydroxymethyl-3-methylpyridine 1.5 g (6.4 mmol) of 5-(2-furylmethylthio)-2-hydroxymethyl-3-methylpyridine (prepared in accordance with Example Ac) are dissolved in 40 ml of acetonitrile, 1.5 g (8.0 mmol) of N,N-dimethylmethyleneimmonium iodide are added and the mixture is stirred at 80° C. for 4 h. After the acetonitrile has been distilled off in vacuo, the residue is treated with water (10 ml), brought to pH 10 using sodium carbonate solution and extracted using ethyl acetate (3×20 ml). The combined organic phases are washed with water, dried over potassium carbonate and concentrated, and the residue is chromatographed on silica gel (dichloromethane/methanol/triethylamine 4/1/0.1). This gives 1.06 g (57%) of the title compound as a yellow oil.

H NMR (CDCl$_3$): ppm 2.13 (s, 3H); 2.25 (s, 6H); 3.42 (s, 2H); 4.19 (s, 2H); 4.68 (s, 2H); 6.10–6.19 (AB system, 2H); 7.15 (d, J=5.4 Hz, 1H); 8.23 (d, 1H).

After dissolution in diethyl ether, addition of hydrochloric acid in ether gives the title compound as the colorless, hygroscopic dihydrochloride. Decomp. from 90° C.

b) 2-Chloromethyl-4-{[(5-dimethylaminomethyl-2-furyl)methyl]thio}-3-methylpyridine dihydrochloride Following the procedure described under Ad), the compound of Example Ca) as the starting material gives the title compound as a crude product which is dissolved in ethanol and further reacted directly. Crystallization from isopropanol yields a crystalline, colorless dihydrochloride; m.p. from 185° C. (decomp.).

The hydrochlorides of the following compounds are obtained analogously, for example as described in Examples Aa) to Ad):

2-chloromethyl-3-methyl-4-(2-thienylmethylthio)pyridine, 2-chloromethyl-3-methyl-4-(3-thienylmethylthio)pyridine, 2-chloromethyl-3-methoxy-4-(2-thienylmethylthio)pyridine, 2-chloromethyl-4-(2-thienylmethylthio)pyridine, 2-chloromethyl-4-(2-furylmethylthio)pyridine, 2-chloromethyl-4-[(3,4-dimethoxy)-2-pyridinyl-methylthio]-3-methylpyridine and 2-chloromethyl-4-[2-pyridinyl-2-ethylthio]-3-methylpyridine.

D) 2-Chloromethyl-4-(2-furylmethylthio)-3-methoxypyridine hydrochloride

Following the procedure described under Aa) to Ac), 4-chloro-3-methoxy-2-methylpyridine N-oxide as the starting material gives the intermediate 4-(2-furylmethylthio)-2-hydroxymethyl-3-methoxypyridine; m.p. 56°–58° C. Chlorination with thionyl chloride following the procedure described in Example Ad) yields the title compound as a beige powder; m.p. 135° C. (decomp.).

Applicability in industry

The outstanding activity of compounds of the formula I and of the salts thereof against Helicobacter bacteria allows them to be used in human medicine as active ingredients for the treatment of diseases caused by Helicobacter bacteria.

The invention therefore furthermore relates to a process for the treatment of mammals, in particular humans, suffering from diseases caused by Helicobacter bacteria. The process comprises administering to the diseased individual a therapeutically active and pharmacologically acceptable amount of one or more compounds of the formula I and/or the pharmacologically acceptable salts thereof.

The invention furthermore relates to the compounds of the formula I and the pharmacologically acceptable salts thereof for use in the treatment of diseases caused by Helicobacter bacteria.

Equally, the invention provides the use of compounds of the formula I and of the pharmacologically acceptable salts thereof for the preparation of drug products employed for controlling diseases which are caused by Helicobacter bacteria.

The invention furthermore relates to drug products for controlling Helicobacter bacteria which comprise one or more compounds of the general formula I and/or the pharmacologically acceptable salts thereof.

Amongst the Helicobacter strains against which the compounds of the formula I have proved to be effective, particular mention must be made of the strain Helicobacter pylori.

The drug products are prepared by processes known per se with which the expert is familiar. As drug products, the pharmacologically active compounds of the formula I and the salts thereof (=active ingredients) are employed either as such or, preferably, in combination with suitable pharmaceutical auxiliaries, for example in the form of tablets, coated tablets, capsules, emulsions, suspensions, gels or solutions, whose content of active ingredients is advantageously between 0.1 and 95%.

As to which auxiliaries are suitable for the drug product formulations desired, this will be known to the expert due to his/her specialist knowledge. Substances which can be used besides solvents, gelling agents, tableting auxiliaries and other excipients for active ingredients are, for example, antioxidants, dispersants, emulsifiers, antifoams, flavorings, preservatives, solubilizers, colorants or permeation promoters and complexing agents (for example cyclodextrins).

The active ingredients can be applied for example parenterally (for example intravenously) or, in particular, orally.

In general, the active ingredients are administered, in human medicine, at a daily dose of approximately 0.2 to 50, preferably 1 to 30, mg/kg of body weight, if appropriate in the form of several, preferably 2 to 6, single doses for achieving the desired result.

An essential aspect of the invention which must be emphasized particularly in this context is the fact that the compounds of the formula I in which n denotes the number 0 have proved to be active against Helicobacter bacteria even when administering doses below those doses which ought to have been employed for inhibiting gastric acid secretion to an extent which suffices for therapeutical purposes.

Biological tests

The compounds of the formula I were tested for their activity against Helicobacter pylori following a modification of the method described by Tomoyuki Iwahi et al. (Antimicrobial Agents and Chemotherapy, 1991, 490–496) using Columbia agar (Oxoid) over a growth period of 4 days. The MIC values listed in Table 2 below were found here for the tested compounds (the compound numbers shown agree with the compound numbers in the description).

TABLE 2

| Compound No. | MIC Value (μg/ml) |
| --- | --- |
| 1 | ≦1.0 |
| 2 | ≦1.0 |
| 5 | ≦1.0 |
| 6 | ≦1.0 |
| 8 | ≦1.0 |

TABLE 2-continued

| Compound No. | MIC Value (μg/ml) |
| --- | --- |
| 12 | ≦1.0 |
| 16 | ≦1.0 |
| 17 | ≦1.0 |
| 18 | ≦1.0 |
| 19 | ≦1.0 |
| 20 | ≦1.0 |

FORMULA SHEET

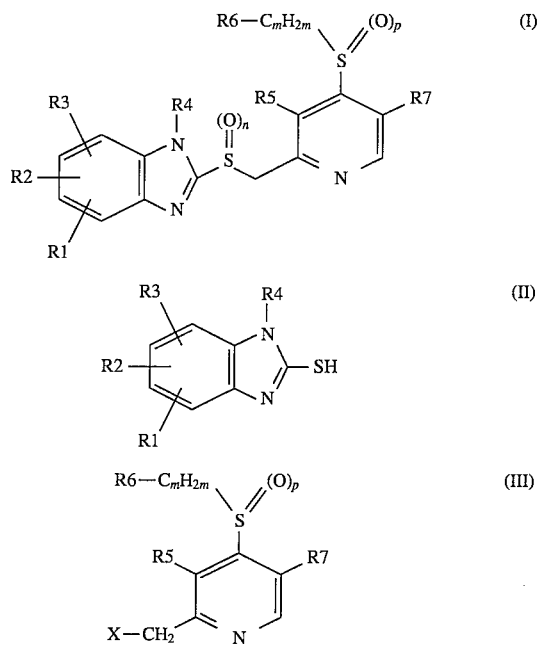

We claim:

1. A compound of the formula I

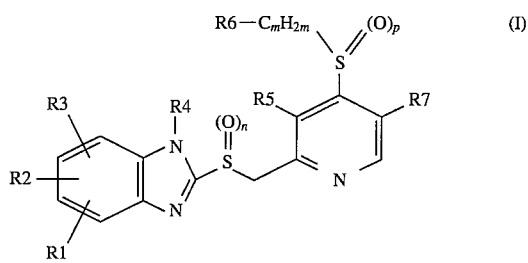

in which

R1 is hydrogen, 1–4C-alkyl or 1–4C-alkoxy,

R2 is hydrogen, 1–4C-alkyl, 1–4C-alkoxy, halogen, trifluoromethyl, fully or predominantly fluorine-substituted 1–4C-alkoxy, chlorodifluoromethoxy, 2-chloro-1,1,2-trifluoroethoxy, or, if desired, together with R3 1–2C-alkylenedioxy which is fully or partially substituted by fluorine, or chlorotrifluoroethylenedioxy, R3 is hydrogen, 1–4C-alkoxy which is fully or predominantly substituted by fluorine, or is chlorodifluoromethoxy, 2-chloro-1,1,2-trifluoroethoxy, or, if desired, together with R2 1–2C-alkylenedioxy which is fully or partially substituted by fluorine, or chlorotrifluoroethylenedioxy, R4 is hydrogen or 1–4C-alkyl, R5 is hydrogen, 1–4C-alkyl or 1–4C-alkoxy, R6 is a heterocycle selected from the group consisting of furan, thiophene, pyrrole, oxazole, isoxazole, thiazole, isothiazole, imidazole, pyrazole, 1,2,3-triazole, 1,2,4-triazole, tetrazole, 1,3,4-thiadiazole, 1,2,4-thiadiazole, pyrimidine and pyridine, each of which is substituted by R8 and R9, R7 is hydrogen, 1–4C-alkyl or 1–4C-alkoxy, R8 is hydrogen, 1–4C-alkyl, 1–4C-alkoxy, halogen, guanidino, 1–4C-alkyl which is substituted by R10, or —N(R11)R12, R9 is hydrogen, 1–4C-alkyl, 1–4C-alkoxy or halogen, R10 is hydroxyl, 1–4C-alkoxy or —N(R11)R12, where R11 is hydrogen, 1–4C-alkyl or —CO—R13 and R12 is hydrogen or 1–4C-alkyl, or where R11 and R12 together and including the nitrogen atom to which both are bonded represent a piperidino or morpholino radical, R13 is hydrogen, 1–4C-alkyl or 1–4C-alkoxy, m is a number from 1 to 7, n is the number 0 or 1 and p is the number 0 or 1, or a salt thereof.

2. A compound of the formula I as claimed in claim 1, in which R6 is a heterocycle selected from the group consisting of furan, thiophene, pyrrole, oxazole, isoxazole, thiazole, isothiazole, imidazole, pyrazole, 1,2,3-triazole, 1,2,4-triazole, tetrazole, 1,3,4-thiadiazole and 1,2,4-thiadiazole, and which is substituted by R8 and R9, or a salt thereof.

3. A compound of the formula I as claimed in claim 1, in which

R1 is hydrogen,

R2 is hydrogen, 1–4C-alkoxy, trifluoromethyl, 1–4C-alkoxy which is fully or predominantly substituted by fluorine, or together with R3 is 1–2C-alkylenedioxy which is fully or partially substituted by fluorine, R3 is hydrogen or together with R2 is 1–2C-alkylenedioxy which is fully or partially substituted by fluorine, R4 is hydrogen, R5 is hydrogen, 1–4C-alkyl or 1–4C-alkoxy, R6 is a heterocycle which is selected from the group consisting of furan, thiophene, thiazole, imidazole and pyridine and which is substituted by R8 and R9, R7 is hydrogen, R8 is hydrogen, 1–4C-alkyl or 1–4C-alkoxy or 1–4C-alkyl which is substituted by R10, R9 is hydrogen or 1–4C-alkoxy, R10 is —N(R11)R12, where R11 is 1–4C-alkyl and R12 is 1–4C-alkyl, m is a number from 1 to 3, n is the number 0 or 1 and p is the number 0, or a salt thereof.

4. A compound of the formula I as claimed in claim 1, in which

R1 is hydrogen,

R2 is hydrogen or methoxy,

R3 is hydrogen,

R4 is hydrogen,

R5 is hydrogen, 1–4C-alkyl or 1–4C-alkoxy,

R6 is a heterocycle which is selected from the group consisting of furan, thiophene, thiazole, imidazole and pyridine and which is substituted by R8 and R9, R7 is hydrogen, R8 is hydrogen, 1–4C-alkyl or 1–4C-alkoxy or 1–4C-alkyl which is substituted by R10, R9 is hydrogen or 1–4C-alkoxy, R10 is —N(R11)R12, where R11 is 1–4C-alkyl and R12 is 1–4C-alkyl, m is a number from 1 to 3, n is the number 0 and p is the number 0, or a salt thereof.

5. A compound of the formula I as claimed in claim 1, in which

R1 is hydrogen,

R2 is hydrogen, halogen, methoxy, difluoromethoxy or trifluoromethyl,

R3 is hydrogen,

R4 is hydrogen,

R5 is hydrogen, 1–4C-alkyl or 1–4C-alkoxy,

R6 is a heterocycle which is selected from the group consisting of furan, thiophene, thiazole, imidazole, pyrrole, oxazole and pyrazole and which is substituted by R8 and R9, R7 is hydrogen, R8 is hydrogen, 1–4C-alkyl, guanidino, 1–4C-alkyl which is substituted by R10, or —N(R11)R12, R9 is hydrogen or 1–4C-alkyl, R10 is —N(R11)R12, R11 is hydrogen, 1–4C-alkyl or —CO—R13, R12 is hydrogen or 1–4C-alkyl, R13 is hydrogen, 1–4C-alkyl or 1–4C-alkoxy, m is a number from 1 to 3, n is the number 0 and p is the number 0, or a salt thereof.

6. A compound of the formula I as claimed in claim 1, in which

R1 is hydrogen,

R2 is hydrogen or methoxy,

R3 is hydrogen,

R4 is hydrogen,

R5 is hydrogen, 1–4C-alkyl or 1–4C-alkoxy,

R6 is a heterocycle which is selected from the group consisting of furan, thiophene, thiazole and imidazole and which is substituted by R8 and R9, R7 is hydrogen, R8 is hydrogen, guanidino, methyl which is substituted by R10, or —N(R11)R12, R9 is hydrogen or 1–4C-alkyl, R10 is —N(R11)R12, R11 is hydrogen, 1–4C-alkyl or —CO—R13, R12 is hydrogen or 1–4C-alkyl, R13 is hydrogen, 1–4C-alkyl or 1–4C-alkoxy, m is the number 1 or 2, n is the number 0 and p is the number 0, or a salt thereof.

7. A process for the preparation of the compounds of the formula I as claimed in claim 1, in which R1, R2, R3, R4, R5, R6, R7, m, n and p are as defined in claim 1, and of the salts thereof, which comprises reacting mercaptobenzimidazoles of the formula II

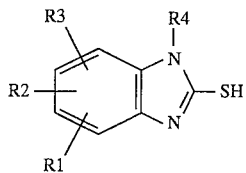

in which R1, R2, R3 and R4 are as defined in claim 1, with picoline derivatives III

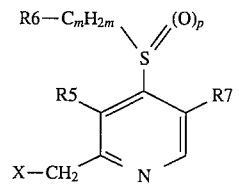

in which R5, R6, R7, m and p are as defined in claim 1 and X is a suitable leaving group, and (if the desired end products are compounds of the formula I where n=1) subsequently oxidizing the resulting 2-benzimidazolyl-2-pyridylmethyl sulfides of the formula I where n=0 and/or, if desired, converting them into the salts.

8. A drug product comprising one or more compounds of the formula I as claimed in claim 1 and/or the pharmacologically acceptable salts thereof.

9. A method of treating a subject afflicted by a condition caused by Helicobacter bacteria, by administering an effective amount of a compound of claim 1 or a pharmacologically acceptable salt thereof.

10. A method of preparing a composition to treat a condition caused by Helicobacter bacteria wherein a compound of claim 1 or a pharmaceutically acceptable salt thereof is combined with a pharmaceutically acceptable diluent.

* * * * *